United States Patent [19]

Steck et al.

[11] Patent Number: 5,002,639
[45] Date of Patent: Mar. 26, 1991

[54] SEPARATION OF ORTHO-, META- AND PARA-TOLUNITRILE FROM TERNARY MIXTURES OF THE ISOMERS

[75] Inventors: Werner Steck, Ludwigshafen; Harald Rust, Neustadt; Helmut Lermer, Ludwigshafen; Fritz Naeumann, Mannheim, all of Fed. Rep. of Germany

[73] Assignee: BASF Aktiengesellschaft, Ludwigshafen, Fed. Rep. of Germany

[21] Appl. No.: 566,677

[22] Filed: Aug. 13, 1990

[30] Foreign Application Priority Data

Aug. 24, 1989 [DE] Fed. Rep. of Germany ....... 3927916

[51] Int. Cl.$^5$ .................. B01D 3/14; C07C 253/34
[52] U.S. Cl. .......................................... 203/48; 203/80; 558/327; 558/328; 558/329; 558/355; 558/356
[58] Field of Search .................................. 203/48, 80; 558/327–329, 355, 356

[56] References Cited

U.S. PATENT DOCUMENTS

| | | | |
|---|---|---|---|
| 1,918,997 | 7/1933 | Weiland | 203/48 |
| 2,499,055 | 2/1950 | Cosby et al. | 558/327 |
| 2,783,266 | 2/1957 | Toland | 558/329 |
| 2,838,558 | 6/1958 | Hadley et al. | 558/327 |
| 3,362,982 | 1/1968 | Oga et al. | 203/48 |
| 3,709,979 | 1/1973 | Chu | 502/77 |

*Primary Examiner*—Wilbur Bascomb
*Attorney, Agent, or Firm*—John H. Shurtleff

[57] ABSTRACT

A process for the separation of ortho-, meta- and para-tolunitrile from ternary mixtures of isomers entails removing ortho-tolunitrile from these mixtures by distillation under pressures of from $10^2$ and $10^5$ Pa and with a reflux ratio of from 1:1 to 200:1, and distilling the remaining binary mixture of meta- and para-tolunitrile to concentrate to more than 75 mol-% para-tolunitrile, and freezing out the paratolunitrile at below 26° C., and a process for the preparation of suitable ternary mixtures of isomers entails isomerization of pure ortho-, meta- or para-tolunitrile or mixtures thereof at from 380° to 580° C. on zeolite catalysts.

9 Claims, No Drawings

SEPARATION OF ORTHO-, META- AND PARA-TOLUNITRILE FROM TERNARY MIXTURES OF THE ISOMERS

The present invention relates to a process for the separation of ortho-, meta- and para-tolunitrile from ternary mixtures of the isomers by a combination of distillation and crystallization by freezing out one component.

The isomerization of methylbenzonitriles (tolunitriles) in the gas phase on an aluminum zeolite of the ZSM-5 type in the acidic H form is disclosed by F. R. Weigert, J. Org. Chem. 51 (1986) 2653–2655. It is stated therein that the thermodynamic equilibrium with 46% ortho-, 34% meta- and 20% para-tolunitrile is set up at 500° C. and with contact times of about 3 seconds, without substantial quantities of byproducts being formed.

Other zeolites such as the wide-pore zeolites HY, H-mordenite and H-omega are said not to catalyze the isomerization.

To date no economic use has been found for any process leading to ternary mixtures of isomers, namely ortho-, meta- and para-tolunitrile. The reason for this is the small difference in boiling points between the three isomeric tolunitriles, which has to date made separation by distillation on the industrial scale appear uneconomic.

Hence it is an object of the present invention to obtain the pure tolunitriles economically from ternary or binary mixtures of them, and to develop a process for the preparation of suitable ternary mixtures as starting material.

We have found that this object is achieved by a process for separating ortho-, meta- and para-tolunitrile from ternary mixtures of isomers, which comprises removing ortho-tolunitrile from these mixtures by distillation under pressures of from $10^2$ to $10^5$ Pa and with a reflux ratio of from 1:1 to 200:1, and distilling the remaining binary mixture of meta- and para-tolunitrile to concentrate to more than 75 mol-% para-tolunitrile, and freezing out the para-tolunitrile at below 26° C. We have additionally found a process for preparing suitable ternary mixtures of isomeric tolunitriles by isomerization of pure ortho-, meta- or para-tolunitrile or mixtures thereof at from 380° to 580° C. on zeolite catalysts.

The distillation (rectification in this case) of the ternary mixture can be carried out continuously or batchwise. It has emerged that operating pressures of from $10^2$ to $10^5$ Pa, preferably from $10^3$ to $3 \times 10^4$ Pa, in particular of $10^4$ Pa, are very suitable for this. Possible columns are those of the prior art, such as packed columns, including those with a longitudinal partition, or plate columns. Very good results are achieved, for example, by continuous workup of the crude ternary mixture in two columns or in one column with a longitudinal partition and an appropriate number of plates.

It has also emerged that a particularly straightforward and economic way of obtaining para-tolunitrile from these mixtures of isomers is by a combination of distillation and crystallization. For this, first the o-tolunitrile is distilled out under pressures of from $10^2$ to $10^5$ Pa, preferably from $10^2$ to $3 \times 10^4$ Pa. The m-tolunitrile is then distilled out of the remaining binary mixture of meta- and para-tolunitrile, likewise under pressures of from $10^2$ to $10^5$ Pa, preferably from $10^2$ to $3 \times 10^4$ Pa, until the remaining mixture contains more than 75, e.g. from 75 to 95, mol-%, preferably more than 80%, para-tolunitrile. It is surprisingly easy to obtain pure para-tolunitrile from such para-rich mixtures by crystallization at from $-25°$ to $+25°$ C., preferably from $-10°$ to 20° C. If necessary, crystallization can also be induced by adding seed crystals. Meta-tolunitrile is enriched in the mother liquor. The crystallization of the para-tolunitrile can be repeated, by melting the crystals and allowing them to recrystallize, as often as needed for the desired purity.

The mixture of the three isomeric tolunitriles required for the separation according to the invention can be prepared by isomerization of pure tolunitriles or any mixtures of two or all of the tolunitrile isomers. Such binary or ternary mixtures are also produced, for example, in the distillation or crystallization according to the invention, and can be recycled for isomerization.

Particularly suitable for the preparation of isomer mixtures has proven to be the gas-phase isomerization of ortho-, meta- and para-tolunitrile or mixtures thereof at from 380° to 580° C. on zeolite catalysts, in particular on aluminosilicate zeolites or gallium silicate zeolites of the pentasil family, because this yields, in only one transit, ternary isomer mixtures whose composition may be near the 46 mol-% ortho, 34 mol-% meta and 20 mol-% para of the thermodynamic equilibrium.

The conditions suitable for the isomerization according to the invention are from 380° to 580° C. The reaction can be carried out, for example, in the gas phase under atmospheric pressure in a fixed or fluidized bed. Good results can be achieved with a WHSV of from 0.1 to 2.5 $h^{-1}$ (units of WHSV=g of feed tolunitrile mixture per g of catalyst and hour). It has proven advantageous to carry out this reaction in the presence of inert gases such as nitrogen or noble gases. Isomerization in the presence of hydrogen may achieve higher conversions at the expense of selectivity.

It is also possible to carry out the isomerization under elevated pressure. In this case, the isomeric tolunitriles may be in the gas or liquid phase or in the supercritical state, depending on the temperature and pressure. A pressure of from $10^5$ to $10^7$ Pa, preferably from $2 \times 10^6$ to $7 \times 10^6$ Pa, can be employed for this reaction.

The isomerization takes place with high selectivity. Byproducts which may be formed are small amounts of toluene, benzonitrile and dimethylbenzonitriles.

The pentasil-type zeolites suitable for the process according to the invention have as secondary structural unit (=secondary building unit, basic unit of the zeolite structure) a five-membered ring composed of $TO_4$ tetrahedrons, possible T cations being Si, Al and Ga. The pentasil zeolites are defined by G. T. Kokotailo and W. M. Meier, Chem. Soc. Spec. Publ. 33 (1980) 133–139. Pentasil zeolites have a high $SiO_2/Al_2O_3$ molar ratio—also called modulus—and have pore sizes between those of type A and of type X or Y zeolites. Pentasil zeolites with $SiO_2/Al_2O_3$ ratios of from 25 to 10,000, for example, have proven very suitable for the process according to the invention. The preparation of these pentasil zeolites is described, inter alia, in U.S. application Ser. Nos. 3,702,886 (ZSM-5), 3 709 979 (ZSM-11), 4 061 724 (Silicalite ®) and 4,073,865. The isotactic pentasil zeolites disclosed in EP-A-0 034 727 also belong with these.

The aluminosilicate zeolite is prepared, for example, from an aluminum compound, preferably $Al(OH)_3$ or $Al_2(SO_4)_3$, and a silicon component such as highly disperse silica, silica gel or silica sol, in aqueous amine solution, in particular in polyamines such as 1,6- diaminohexane or 1,3-diaminopropane or triethylenetetramine solution with or without addition of alkali metal or alkaline earth metal, at from 100° to 220° C. under autogenous pressure. The resulting aluminosilicate zeolites have an $SiO_2/Al_2O_3$ ratio of from 15 to 10,000, depending on the chosen amounts of starting materials.

Aluminosilicate zeolites of these types can also be synthesized in an ether such as diethylene glycol dimethyl ether, in an alcohol such as methanol or 1,4-butanediol or in water.

Also suitable are gallium silicate zeolites or zeolites which contain both gallium and aluminum as trivalent lattice ion.

Finely divided zeolites whose crystals do not exceed about 3 μm in size and are preferably smaller than about 1.5 μm have proven very suitable for rapid attainment of equilibrium in the tolunitrile isomerization. The crystal size can easily be determined by conventional transmission (TEM) or scanning (SEM) electron microscopy.

The zeolite powders resulting after their synthesis, isolation, drying at from 100° to 160° C. and calcination at from 450° to 550° C. can be shaped with a binder in the ratio by mass of zeolite to binder of from 90:10 to 40:60 into, for example, extrudates or pellets. Suitable binders are various aluminas, preferably boehmite, amorphous aluminosilicates with an $SiO_2/Al_2O_3$ ratio of from 25:75 to 90:10, $SiO_2$, $TiO_2$, mixtures of highly disperse $SiO_2$ and highly disperse $Al_2O_3$, and clay. After the extrudates or pellets have been shaped they are dried at 110° C. and calcined at around 500° C.

Very suitable catalysts are also obtained when the isolated zeolite is shaped immediately after drying and subjected to calcination only after shaping. The pentasil zeolites can be employed in pure form, without binder, as extrudates or pellets, examples of extrusion or peptization agents which can be used being ethylcellulose, stearic acid, potato starch, formic acid, oxalic acid, acetic acid, nitric acid, ammonia, amines and graphite or mixtures thereof.

If, by reason of the mode of its preparation, the zeolite is not in the catalytically active, acidic H form but, for example, in the Na form, the latter can be converted completely or partially into the desired H form by ion exchange, e.g. with ammonium ions, and subsequent calcination or by treatment with acids.

If inactivation caused by deposition of carbon occurs when the zeolite catalysts are used according to the invention, it is advisable to regenerate the zeolites by burning off the carbon with air or with an air/$N_2$ mixture at from 400° to 550° C. This usually returns the zeolites to their initial activity.

It may be advantageous, in order to achieve maximum selectivity, high conversion and long useful lives, to modify the zeolites in such a way that the content of modifying elements ensures adequate activity of the catalysts.

An example of suitable modification of the catalysts is to dope the shaped or unshaped zeolites with metal salts by ion exchange or impregnation. Examples of metals which are used are rare earth metals such as lanthanum and/or cerium, or noble metals such as Pd.

The doping is expediently carried out in such a way that, for example, the shaped zeolite is placed in an ascending tube and, for example, an aqueous or ammoniacal solution of a halide or nitrate of the metals described above is passed over it at from 20° to 100° C. Ion exchange of this type can be applied, for example, to the hydrogen, ammonium or alkali metal form of the zeolite. Another way of applying metal to the zeolite is to impregnate it, for example, with a halide, a nitrate, a carbonate or an oxide of the metals described above in aqueous, alcoholic or ammoniacal solution. Both ion exchange and impregnation will be followed by at least one drying, and possibly another calcination.

Another possibility for the modification comprises treating the zeolite, before or after it has been shaped, with acids such as hydrochloric acid, hydrofluoric acid and phosphoric acid and/or steam. This entails, for example, treating powdered zeolites with 1 N phosphoric acid at 80° C. for 1 h. The treatment is followed by washing with water, drying at 110° C. for 16 h and calcining at, for example, 500° C. for 10 hours.

The catalysts described below can be employed as 2- to 4-mm extrudates or as pellets of diameter 3 to 5 mm or as particles of size from 0.1 to 0.5 mm or as material in a fluidized bed.

The pure tolunitrile isomers are required as starting materials and intermediates for a large number of organic syntheses (Rompps Chemie-Lexikon; 8th Edition, 1988, page 4290) and as solvents for various purposes as disclosed in U.S. application Ser. No. 3,231,600, column 1, 2nd paragraph.

PREPARATION OF THE CATALYSTS

Catalysts 1 and 2

Commercial ZSM-5 catalysts in the H form with the following properties were employed:

| Catalyst | $SiO_2/Al_2O_3$ | Crystal size [μm] |
| --- | --- | --- |
| 1 | 57 | 0.75 |
| 2 | 57 | <0.05 |

Catalyst 3

A gallium silicate zeolite of the pentasil type is prepared in a hydrothermal synthesis from 1730 g of highly disperse $SiO_2$, 469 g of sodium gallate solution (12.7% by weight $Ga_2O_3$, 12.2% by weight Na), 6000 g of aqueous 1,6-diaminohexane solution (50% by weight amine) and 21,000 g of water at 150° C. under autogenous pressure in a stirred autoclave. The crystalline reaction product is filtered off and washed and then dried at 100° C. for 24 h and calcined at 500° C. for 24 h. This gallium silicate zeolite contains 91.9% by weight $SiO_2$ and 3.06% by weight $Ga_2O_3$. The crystal size is <0.1 μm.

This material is used to prepare, by shaping with pyrogenic silica (8:2 parts by mass) and a shaping auxiliary, 2 mm extrudates which are dried at 110° C. for 16 h and calcined at 500° C. for 16 h.

The extrudates are subjected to four exchanges with 20% by weight $NH_4Cl$ solution (15 ml of solution per g of shaped articles) at 80° C. in an ascending tube. They are subsequently washed free of chloride. The extrudates are dried at 110° C. for 10 h and then calcined at 500° C. for 5 h. The Na content is then 0.0045% by weight.

Catalyst 4

An aluminosilicate zeolite of the ZSM-5 type is prepared under hydrothermal conditions and autogenous pressure at 160° C. from 1500 g of pyrogenic silica, 84 g of aluminum sulfate 18-hydrate, 240 g of sodium hydroxide, 980 g of tetra-n-propylammonium bromide and 18,000 g of water in a stirred autoclave. The crystalline reaction product is filtered off and washed and then dried at 110° C. for 24 h and calcined at 500° C. for 24 h. This zeolite has the following composition: 85.4% by weight $SiO_2$, 1.00% by weight $Al_2O_3$, 0.75% by weight Na. The crystal size is 2 μm.

This zeolite is used to prepare, by shaping with a shaping auxiliary, 2 mm extrudates which are dried at 110° C. for 16 h and calcined at 500° C. for 16 h.

The extrudates are subjected to four exchanges with 20% by weight $NH_4Cl$ solution (15 ml of solution per g of shaped articles) at 80° C. in an ascending tube. They are subsequently washed free of chloride. The extrudates are dried at 110° C. for 10 h and then calcined at 500° C. for 5 h. The Na content is then 0.015% by weight.

Catalyst 5

An aluminosilicate zeolite of the ZSM-5 type is prepared under hydrothermal conditions and autogenous pressure at 175° C. from 1000 g of pyrogenic silica, 48 g of sodium aluminate (58.6% by weight $Al_2O_3$, 40.0% by weight $Na_2O$), 44 g of sodium hydroxide, 1690 g of aqueous tetra-n-propylammonium hydroxide solution (20% strength) and 16,600 g of water in a stirred autoclave. The crystalline reaction product is filtered off and washed and then dried at 110° C. for 24 h and calcined at 500° C. for 24 h. This zeolite has the following composition: 85.8% by weight $SiO_2$, 2.3% by weight $Al_2O_3$, 0.40% by weight Na. The crystal size is 3 μm.

This material is used to prepare, by shaping with pyrogenic silica (8:2 parts by mass) and a shaping auxiliary, 2 mm extrudates which are dried at 110° C. for 16 h and calcined at 500° C. for 16 h.

The extrudates are subjected to four exchanges with 20% by weight $NH_4Cl$ solution (15 ml of solution per g of shaped articles) at 80° C. in an ascending tube. They are subsequently washed free of chloride. The extrudates are dried at 110° C. for 10 h and then calcined at 500° C. for 5 h. The Na content is then 0.002% by weight.

Catalyst 6

An aluminosilicate zeolite of the ZSM-11 type is prepared under hydrothermal conditions and autogenous pressure at 160° C. from 10,900 g of water, 6,300 g of sodium waterglass (8.0% by weight $Na_2O$, 26.5% by weight $SiO_2$, 180 g of aluminum sulfate 18-hydrate, 600 g of conc. sulfuric acid and 600 g of 1,8-diaminooctane in a stirred autoclave. The crystalline reaction product is filtered off and washed and then dried at 110° C. for 24 h and calcined at 500° C. for 24 h.

This material is used to prepare, by shaping with pseudoboehmite (6:4 parts by mass), 2 mm extrudes which are dried at 110° C. for 16 h and calcined at 500° C. for 16 h.

The extrudates are subjected to four exchanges with 20% by weight $NH_4Cl$ solution (15 ml of solution per g of shaped articles) at 80° C. in an ascending tube. They are then washed free of chloride. The extrudates are dried at 110° C. for 10 h and then calcined at 500° C. for 5 h. The Na content is then 0.0026% by weight.

Catalyst 7

An aluminosilicate zeolite of the pentasil type is prepared under hydrothermal conditions and autogenous pressure at 150° C. from 650 g of highly disperse $SiO_2$, 203 g of $Al_2(SO_4)_3 \times 18\ H_2O$ in 11,300 g of an aqueous 1,6-diaminohexane solution (42% by weight amine) in a stirred autoclave. The crystalline reaction product is filtered off and washed and then dried at 110° C. for 24 h and calcined at 500° C. for 24 h. This aluminosilicate zeolite contains 92.6% by weight $SiO_2$ and 4 6% by weight $Al_2O_3$. The crystal size is 0.25 μm.

This material is used to prepare, by shaping with a shaping auxiliary, 2 mm extrudates which are dried at 110° C. for 16 h and calcined at 500° C. for 16 h.

The extrudates are impregnated with an aqueous $Ce(NO_3)_3 \times 6\ H_2O$ solution, dried at 130° C. for 2 h and calcined at 540° C. for 2 h. The Ce content is 1.6% by weight.

Catalyst 8

The undoped extrudates of catalyst 7 are impregnated with an aqueous $La(NO_3)_3 \times 6\ H_2O$ solution, dried at 130° C. for 2 h and calcined at 540° C. for 2 h. The La content is 1.8% by weight.

Catalyst 9 A

An aluminosilicate zeolite of the pentasil type is prepared under hydrothermal conditions and autogenous pressure at 184° C. from 700 g of highly disperse $SiO_2$ and 196 g of $Al_2(SO_4)_3 \times 18\ H_2O$ in 12.2 kg of an aqueous triethylenetetramine solution (38% by weight amine) in a stirred autoclave. The crystalline reaction product is filtered off and washed and then dried at 110° C. for 24 h and calcined at 500° C. for 24 h. This aluminosilicate zeolite contains 92.9% by weight $SiO_2$ and 3.8% by weight $Al_2O_3$. The crystal size is 8.5 μm.

This material is used to prepare, by shaping with a shaping auxiliary, 2 mm extrudates which are dried at 110° C. for 16 h and calcined at 500° C. for 16 h.

Catalyst 9 B

The undoped extrudates of catalyst 9A are impregnated with an aqueous $Pd(NO_3)_2$ solution, dried at 130° C. for 1 h and calcined at 540° C. for 1 h. The Pd content is 2.05% by weight.

Catalyst 10

A molecular sieve of the Silicalite type is prepared under hydrothermal conditions and autogenous pressure at 160° C. from 2250 g of pyrogenic silica, 324 g of sodium hydroxide, 1500 g of tetra-n-propylammonium bromide and 27,000 g of water in a stirred autoclave. The crystalline reaction product is filtered off and washed and then dried at 110° C. for 24 h and calcined at 500° C. for 24 h. This molecular sieve has the following composition: 95.5% by weight $SiO_2$, 0.0020% by weight $Al_2O_3$. The crystal size is 6 μm.

This molecular sieve is used to prepare, by shaping with a shaping auxiliary, 2 mm extrudates which are dried at 110° C. for 16 h and calcined at 500° C. for 16 h. The extrudates are subjected to four exchanges with 20% by weight NH Cl solution (15 ml of solution per g of shaped articles) at 80° C. in an ascending tube. They are subsequently washed free of chloride. The extrudates are dried at 110° C. for 10 h and then calcined at 500° C. for 5 h. The Na content is then 0.09% by weight.

CATALYSTS FOR COMPARATIVE EXAMPLES

Catalyst 11

Catalyst 11 is a commercial $Al_2O_3$ (D 10-10 ®)

Catalyst 12

Catalyst 12 is a commercial $SiO_2$ (D 11-10 ®)

Catalyst 13

Commercial ZEOLON 900 H mordenite from Norton.

Catalyst 14

Commercial US-Y zeolite in the H form

Catalyst 15

A SAPO-11 is synthesized by homogeneously mixing 200 g of orthophosphoric acid (98% by weight) with 417 g of aluminum triisopropylate and 60 g of silica sol (30% by weight $SiO_2$) in 927 g of water; 91.5 g of di-n-propylamine are added to this mixture. Reaction is then carried out at 200° C. under autogenous pressure in a stirred autoclave for 96 h. The silicon aluminum phosphate is filtered off and washed and then dried at 110° C. and calcined at 500° C. The composition of the SAPO-11 is 40.4% by weight $Al_2O_3$, 49.5% by weight $P_2O_5$ and 1.87% by weight $SiO_2$. The crystal size is below 0.5 μm.

This material is used to prepare, by shaping with a shaping auxiliary, 2 mm extrudates which are dried at 110° C. for 16 h and calcined at 500° C. for 16 h.

TECHNICAL AND PHYSICAL DATA ON THE TOLUNITRILES

TABLE I

Boiling points of the tolunitriles under atmospheric pressure in °C.

| | | |
|---|---|---|
| ortho | 205 | CRC Handbook of Chemistry and Physics 68th Edition |
| meta | 213 | CRC Handbook of Chemistry and Physics 68th Edition |
| para | 218 | CRC Handbook of Chemistry and Physics 68th Edition |

TABLE II

Melting points of the tolunitriles (MW 117.2)

| | m.p. [°C.] | Source |
|---|---|---|
| ortho | −13.5 | CRC Handbook of Chemistry and Physics 68th Edition |
| meta | −23 | CRC Handbook of Chemistry and Physics 68th Edition |
| para | 29.5 | CRC Handbook of Chemistry and Physics 68th Edition |

I. ISOMERIZATION OF TOLUNITRILES

Examples 1 to 18

Gas-phase isomerization of tolunitriles

The gas-phase reactions were carried out under isothermal conditions and atmospheric pressure in a tube reactor (spiral, 0.6 cm internal diameter, length from 90 cm to 180 cm) with a single transit or several transits, circulating the gas, on a fixed bed of catalyst at from 400° to 550° C. The reaction products were characterized by conventional techniques (GC/MS, NMR or boiling point).

To prepare suitable mixtures of isomers in the tube reactor described above, the starting materials, e.g. o-tolunitrile, are continuously fed under atmospheric pressure by means of a metering pump, with simultaneous introduction of nitrogen as inert gas, into the reactor where, before they reach the catalyst bed, they are vaporized and then pass as gases over the catalyst.

The gaseous precursors and reaction products are passed either in the ascending or descending mode through the fixed bed catalyst. In the procedure with a single transit (reaction type 1), a WHSV of from about 0.2 to 2 $h^{-1}$ is suitable, for example. In the circulating procedure (reaction type 2) from 15 to 25 g of catalyst were used in the fixed bed, for example. From 30 to 50 ml of tolunitrile were placed in a glass flask and then the tolunitrile was circulated at 50 ml/h by a metering pump and vaporized before each passage through the fixed bed catalyst.

After the isomerization is complete, the discharge from the reactor is condensed and analyzed by gas chromatography after the running time stated in hours (h). The conversions and selectivities are indicated in the tables in percentage areas. The abbreviation for tolunitrile is TN.

R type = reaction type, 1 = single passage; 2 = circulating procedure; T = temperature; C = comparative example.

Essentially the only byproducts detected were benzonitrile, dimethylbenzonitriles and toluene.

(A) Isomerization of o-tolunitrile
(B) Isomerization of m-tolunitrile
(C) Isomerization of a binary mixture of 50% o-tolunitrile and 50% m-tolunitrile
(D) Isomerization of ternary mixtures of isomers produced by distillation (Examples 20 to 22).

The results are compiled in Tables A to D.

TABLE A

| | Catalyst | | | running time in | T | Conversion | Selectivity | | |
|---|---|---|---|---|---|---|---|---|---|
| Example | no. | weight [g] | R type | h | [#C] | o-TN | m-TN | p-TN | m + p |
| 1 | 2 | 4 | 1 | 2 | 500 | 15.3 | 71.4 | 11.2 | 82.6 |
| 2 | 2 | 20 | 1 | 2 | 500 | 55.0 | 53.9 | 27.2 | 81.6 |
| | | | | 12 | 500 | 33.1 | 75.4 | 22.1 | 96.5 |
| | regenerated 2x at 500#C | | | 2 | 500 | 55.6 | 54.3 | 28.6 | 82.9 |
| | | | | 6 | 500 | 44.0 | 67.2 | 27.5 | 94.7 |
| C1 | 14 | 4 | 1 | 2 | 500 | 1.7 | 44.5 | 2.9 | 47.4 |
| 3 | 2 | 20 | 2 | 6 | 500 | 49.2 | 60.0 | 27.8 | 87.8 |
| | | | | 22 | | 55.2 | 56.8 | 30.3 | 87.1 |
| 4 | 2 | 20 | 2 | 5 | 400 | 19.0 | 65.3 | 24.3 | 85.6 |

TABLE A-continued

Isomerization of o-tolunitrile

| Example | Catalyst no. | weight [g] | R type | running time in h | T [°C] | Conversion o-TN | Selectivity m-TN | p-TN | m + p |
|---|---|---|---|---|---|---|---|---|---|
|  |  |  |  | 21 |  | 29.4 | 68.0 | 22.4 | 90.4 |
| 5 | 1 | 20 | 2 | 2 | 500 | 46.8 | 60.0 | 29.9 | 89.9 |
|  |  |  |  | 18 |  | 57.2 | 54.9 | 30.9 | 85.8 |
| 6 | 3 | 20 | 2 | 17 | 500 | 54.0 | 39.5 | 14.5 | 54.0 |
| 7 | 4 | 20 | 2 | 23 | 500 | 52.9 | 58.6 | 31.4 | 90.0 |
| 8 | 5 | 20 | 2 | 22 | 500 | 49.1 | 57.6 | 28.5 | 86.1 |
| 9 | 6 | 20 | 2 | 23 | 500 | 48.3 | 46.2 | 30.2 | 94.6 |
| 10 | 7 | 20 | 2 | 21 | 500 | 29.5 | 74.8 | 16.9 | 91.7 |
| 11 | 8 | 20 | 2 | 22 | 500 | 28.8 | 73.8 | 16.3 | 90.5 |
| 12 | 9A | 20 | 2 | 17 | 500 | 31.4 | 59.5 | 30.9 | 90.4 |
| 13 | 9B | 20 | 2 | 22 | 500 | 19.9 | 59.4 | 30.8 | 91.2 |
| 14 | 10 | 20 | 2 | 23 | 500 | 14.6 | 58.0 | 30.2 | 88.2 |
| C2 | 11 | 20 | 2 | 23 | 500 | 6.9 | 5.8 | 0.7 | 6.5 |
| C3 | 12 | 20 | 2 | 71 | 500 | 2.9 | 46.9 | 10.8 | 57.8 |
| C4 | 13 | 20 | 2 | 21 | 500 | 10.3 | 54.2 | 11.1 | 55.3 |
| C5 | 14 | 20 | 2 | 21 | 500 | 2.5 | 26.9 | 0.0 | 26.9 |
| C6 | 15 | 20 | 2 | 23 | 500 | 6.8 | 55.5 | 18.2 | 78.5 |

TABLE B

Isomerization of m-tolunitrile

| Example | Catalyst no. | weight [g] | R type | running time in h | T [°C] | Conversion m-TN | Selectivity o-TN | p-TN | o + p |
|---|---|---|---|---|---|---|---|---|---|
| 15 | 9 | 20 | 2 | 17 | 510 | 50.0 | 45.7 | 45.1 | 90.8 |

TABLE C

Isomerization of a binary mixture of 50% o-tolunitrile and 50% m-tolunitrile
All analytical data in percentage areas

| Example | Catalyst no. | weight [g] | R type | running time in h | T [°C] | o-TN | m-TN | p-TN | m + p to |
|---|---|---|---|---|---|---|---|---|---|
| 16 | 9 | 22 | 2 | starting material | — | 50.0 | 50.0 | 00.0 | 100.0 |
|  |  |  |  | 17 | 490 | 49.1 | 33.9 | 13.6 | 99.0 |

TABLE D

Isomerization of ternary mixtures of isomers produced by distillation (Examples 20 to 23).
All analytical data are percentage areas

| Example | Catalyst no. | weight [g] | R type | running time in h | T [°C] | o-TN | m-TN | p-TN | m + p to |
|---|---|---|---|---|---|---|---|---|---|
| 17 | 2 | 20 | 2 | starting material | — | 89.8 | 10.0 | 0.2 | 100.0 |
|  |  |  |  | 1 | 500 | 58.9 | 30.4 | 8.4 | 97.7 |
|  |  |  |  | 4 |  | 39.9 | 39.2 | 17.0 | 96.1 |
|  |  |  |  | 20 |  | 33.2 | 43.3 | 18.8 | 95.3 |
| 18 | 2 | 20 | 2 | starting material | — | 80.6 | 0.2 | 19.2 | 100.0 |
|  |  |  |  | 6 | 500 | 33.1 | 40.0 | 19.6 | 92.7 |
|  |  |  |  | 22 |  | 31.9 | 42.3 | 17.9 | 92.1 |

Example 19

Liquid-phase isomerization under superatmospheric pressure 5 g of catalyst no. 2 (commercial ZSM-5) in the form of particles from 0.1 to 0.5 mm in size were introduced into a tube reactor of diameter 9 mm and length 25 cm. The catalyst was first heated at 450° C. in a stream of nitrogen for one hour. The reactor outlet was then switched to an overflow valve ($5 \times 10^6$ Pa), the reactor was filled with ortho-tolunitrile by a pump, and then o-tolunitrile was passed at 15 g/h over the catalyst at 450° C. for two hours, collecting the discharged product and analyzing it by gas chromatography.

The results are compiled in Table E.

TABLE E

| Example no. | Catalyst weight [g] | running time in h | T [°C] | Conversion o-TN | Selectivity m-TN | p-TN | m + p |
| --- | --- | --- | --- | --- | --- | --- | --- |
| 19 | 2 | 5 | 2 | 450 | 21.8 | 64.8 | 15.2 | 80 |

II. Distillation of mixtures of isomers to obtain the tolunitriles

C. Examples 20 to 22
Rectification of tolunitrile isomers

Example 20

980 g of a crude mixture containing about 0.2% benzonitrile, 75% o-tolunitrile, 14.8% m-tolunitrile and 10% p-tolunitrile were fractionated in a packed column (glass, 140 cm long, 25 mm diameter, packed with coils of stainless steel wire mesh of diameter 3 mm; the theoretical number of plates is about 20 to 30) under $10^4$ Pa or $10^3$ Pa with a reflux ratio of 30:1. The reduction in the operating pressure towards the end of the distillation from $10^4$ to $10^3$ Pa was intended to prevent temperature-dependent reactions.

The results are compiled in Table F.

Concentration data are percentage areas from the GC.

Example 21

996 g of a crude mixture containing about 0.3% benzonitrile, 45.7% o-tolunitrile, 33.7% m-tolunitrile and 20.2% p-tolunitrile were fractionated in the same column as in Example 20. It emerged that the main parameters responsible for the separation, such as the minimum reflux ratio, cross-sectional loading and separation efficiency, must not be in the threshold region otherwise, as evident in this case, the separation does not meet specifications. Results are compiled in Table G. Concentration data are percentage areas from the GC.

TABLE G

| Fraction no. | Pressure Pa | Temperature Bottom | Temperature Top | Weight g | Weight Total g | Proportionate masses % | Proportionate masses Total % | Benzo-nitrile | o-tolunitrile | m-tolunitrile | p-tolunitrile |
| --- | --- | --- | --- | --- | --- | --- | --- | --- | --- | --- | --- |
| Starting mixture | | | | | | | | 0.3 | 45.7 | 33.7 | 20.3 |
| 1 | $10^4$ | 143 | 130 | 14.0 | 14.0 | 1.41 | 1.41 | 14.6 | 79.3 | 1.7 | 0.6 |
| 2 | $10^4$ | 143 | 125 | 219.0 | 233.0 | 21.99 | 23.39 | 0.6 | 98.9 | 0.3 | 0.06 |
| 3 | $10^4$ | 142 | 125 | 197.0 | 430.0 | 19.78 | 43.17 | — | 99.7 | 0.2 | 0.06 |
| 4 | $10^4$ | 142 | 131 | 38.0 | 486.0 | 3.82 | 46.99 | — | 52.6 | 47.3 | — |
| 5 | $10^4$ | 143 | 132 | 30.0 | 498.0 | 3.01 | 50.00 | — | 11.1 | 88.8 | 0.02 |
| 6 | $10^4$ | 143 | 132 | 87.0 | 585.0 | 8.73 | 58.73 | — | 2.1 | 97.7 | 0.2 |
| 7 | $10^4$ | 145 | 132 | 47.0 | 632.0 | 4.72 | 63.45 | — | 0.3 | 99.4 | 0.3 |
| 8 | $10^3$ | 113 | 62 | 87.0 | 719.0 | 8.73 | 72.19 | — | — | 88.8 | 11.2 |
| 9 | $10^3$ | 113 | 62 | 36.0 | 755.0 | 3.61 | 75.80 | — | — | 76.2 | 23.6 |
| 10 | $10^3$ | 113 | 64 | 99.0 | 854.0 | 9.94 | 85.74 | — | — | 43.9 | 56.0 |
| 11 | $10^3$ | 129 | 64 | 45.0 | 899.0 | 4.52 | 90.26 | — | — | 10.5 | 89.5 |
| 12 | $10^3$ | 200 | 64 | 65.0 | 964.0 | 6.53 | 96.79 | — | — | 5.2 | 94.7 |
| Residue | | | | 32.0 | 996.0 | 3.21 | 100.0 | — | — | 1.8 | 97.9 |

TABLE F

| Fraction no. | Pressure Pa | Temperature Bottom | Temperature Top | Weight g | Weight Total g | Proportionate masses % | Proportionate masses Total % | Benzo-nitrile | o-tolunitrile | m-tolunitrile | p-tolunitrile |
| --- | --- | --- | --- | --- | --- | --- | --- | --- | --- | --- | --- |
| Initial sample | | | | | | | | 0.2 | 75.0 | 14.8 | 10.0 |
| 1 | $10^4$ | 143 | 128 | 24.0 | 24.0 | 2.45 | 2.45 | 9.1 | 89.9 | 0.8 | — |
| 2 | $10^4$ | 142 | 129 | 63.0 | 87.0 | 6.43 | 8.88 | 0.9 | 98.6 | 0.5 | — |
| 3 | $10^4$ | 141 | 129 | 88.0 | 175.0 | 8.98 | 17.86 | 0.03 | 99.6 | 0.3 | — |
| 4 | $10^4$ | 141 | 128 | 207.0 | 382.0 | 21.12 | 38.98 | — | 99.9 | 0.1 | — |
| 5 | $10^4$ | 143 | 126 | 239.0 | 621.0 | 24.39 | 63.37 | — | 99.9 | 0.02 | — |
| 6 | $10^4$ | 142 | 127 | 91.0 | 712.0 | 9.39 | 72.65 | — | 100.0 | — | — |
| 7 | $10^4$ | 142 | 129 | 23.0 | 735.0 | 2.35 | 75.0 | — | 95.6 | 4.3 | 0.3 |
| 8 | $10^4$ | 144 | 133 | 51.0 | 786.0 | 5.20 | 80.20 | — | 10.0 | 89.3 | 0.1 |
| 9 | $10^4$ | 210 | 132 | 50.0 | 836.0 | 5.10 | 85.31 | — | 0.07 | 99.2 | 0.7 |
| 10 | $10^3$ | 146 | 81 | 42.0 | 878.0 | 4.29 | 89.59 | — | 0.2 | 80.6 | 19.2 |
| 11 | $10^3$ | 200 | 82 | 29.0 | 907.0 | 2.96 | 92.55 | — | — | 40.2 | 59.8 |
| Residue | | | | 73.0 | 980.0 | 7.45 | 100.0 | — | — | 1.2 | 98.6 |

Result: At least 99% of the components in the initial mixture are distilled through the column in the sequence of their boiling points. The residue contains p-tolunitrile which is more than 98% pure and can be further purified by crystallization if necessary. There is necessarily a decrease in the proportions of mixed fractions as the separation efficiency of the column increases.

Example 22

1938 g of crude mixture with the same composition as in Example 20 were fractionated in the same column as in Example 1. The results of the analyses on the fractions show optimal separation of the isomeric tolunitriles.

The results are compiled in Table H. Concentration data are percentage areas from the GC.

TABLE H

| Fraction no. | Pressure Pa | Temperature Bottom | Temperature Top | Weight g | Weight Total g | Proportionate masses % | Proportionate masses Total % | Benzo-nitrile | o-tolunitrile | m-tolunitrile | p-tolunitrile |
|---|---|---|---|---|---|---|---|---|---|---|---|
| Initial sample | | | | | | | | 0.3 | 45.7 | 33.7 | 20.3 |
| 1 | $10^4$ | 138 | 126 | 49.0 | 49.0 | 2.53 | 2.53 | 5.9 | 93.2 | — | — |
| 2 | $10^4$ | 141 | 116 | 74.0 | 123.0 | 3.82 | 6.35 | 2.7 | 96.9 | — | — |
| 3 | $10^4$ | 140 | 126 | 77.0 | 200.0 | 3.97 | 10.32 | 1.3 | 98.3 | — | — |
| 4 | $10^4$ | 141 | 126 | 86.0 | 286.0 | 4.44 | 14.76 | 0.3 | 99.3 | — | — |
| 5 | $10^4$ | 140 | 126 | 77.0 | 363.0 | 3.97 | 18.73 | — | 99.7 | — | — |
| 6 | $10^4$ | 142 | 126 | 82.0 | 445.0 | 4.23 | 22.96 | — | 100.0 | — | — |
| 7 | $10^4$ | 142 | 128 | 83.0 | 528.0 | 4.28 | 27.24 | — | 100.0 | — | — |
| 8 | $10^4$ | 142 | 128 | 92.0 | 620.0 | 4.75 | 31.99 | — | 100.0 | — | — |
| 9 | $10^4$ | 142 | 128 | 96.0 | 716.0 | 4.95 | 36.95 | — | 100.0 | — | — |
| 10 | $10^4$ | 142 | 130 | 97.0 | 813.0 | 5.01 | 41.95 | — | 98.2 | 1.8 | — |
| 11 | $10^4$ | 142 | 133 | 89.0 | 902.0 | 4.59 | 46.54 | — | 42.4 | 57.6 | — |
| 12 | $10^4$ | 144 | 134 | 79.0 | 981.0 | 4.08 | 50.62 | — | 7.8 | 91.9 | 0.2 |
| 13 | $10^4$ | 144 | 134 | 82.0 | 1063.0 | 4.23 | 54.85 | — | 1.4 | 98.2 | 0.4 |
| 14 | $10^4$ | 145 | 134 | 93.0 | 1156.0 | 4.80 | 59.65 | — | 0.2 | 99.2 | 0.5 |
| 15 | $10^4$ | 146 | 134 | 104.0 | 1260.0 | 5.37 | 65.02 | — | — | 99.3 | 0.7 |
| 16 | $10^4$ | 146 | 133 | 91.0 | 1351.0 | 4.70 | 69.71 | — | — | 98.3 | 1.7 |
| 17 | $10^4$ | 145 | 135 | 97.0 | 1448.0 | 5.01 | 74.72 | — | — | 93.0 | 6.9 |
| 18 | $10^4$ | 145 | 136 | 90.0 | 1538.0 | 4.64 | 79.36 | — | — | 41.6 | 58.4 |
| 19 | $10^4$ | 144 | 136 | 20.0 | 1558.0 | 1.03 | 80.39 | — | — | 9.8 | 90.1 |
| 20 | $10^4$ | 154 | 136 | 126.0 | 1684.0 | 6.50 | 86.89 | — | — | 1.6 | 98.4 |
| 21 | $10^4$ | 215 | 136 | 58.0 | 1742.0 | 2.99 | 89.89 | — | — | — | 100.0 |
| Residue | | | | 105.0 | 1847.0 | 5.42 | 95.30 | — | — | — | >99.5 |
| Hold up | | | | 91.0 | 1938.0 | 4.70 | 100.0 | — | — | — | — |

III. CRYSTALLIZATION TO OBTAIN TOLUNITRILES

Example 24

The distillation resulted in a starting material composed of 16.6% m-tolunitrile and 83.4% p-tolunitrile. The binary mixture was maintained at 15° C. for 12 h, and then the crystals were separated off and found to be composed of 97.9% p-tolunitrile and 2.1% m-tolunitrile. A trial at 5° C. resulted in crystals comprising 97.3% p-tolunitrile and 2.7% m-tolunitrile.

Example 25

Two binary mixtures of m- and p-tolunitrile obtained from the distillation were crystallized at 22° C., and both the resulting crystals and the mother liquor were analyzed by GC.

The results are compiled in Table K.

TABLE K

| Composition | m-tolunitrile [%] | p-tolunitrile [%] |
|---|---|---|
| starting mixture 1 | 10.5 | 89.5 |
| crystals | 0.9 | 99.1 |
| mother liquor | 15.1 | 84.9 |
| starting mixture 2 | 5.2 | 94.8 |
| crystals | 0.3 | 99.7 |
| mother liquor | 15.1 | 93.9 |

Example 26

A liquid mixture of 90% p-tolunitrile and 10% m-tolunitrile was completely crystallized by cooling to 0° C. and then the resulting crystals were slowly warmed, over the course of 12 hours, to 20° C. During this, part of the crystals melted, forming a mother liquor. The crystals were separated from the mother liquor, and both were analyzed by gas chromatography.

The results are compiled in Table L.

TABLE L

| | m-tolunitrile | p-tolunitrile |
|---|---|---|
| crystals | 0.9% | 99.1% |
| mother liquor | 14.9% | 85.1% |

We claim:

1. A process for separating ortho-, meta- and para-tolunitrile from ternary mixtures of these isomers, which comprises removing ortho-tolunitrile from these mixtures by distillation under pressures of from $10^2$ to $10^5$ Pa and with a reflux ratio of from 1:1 to 200:1, and distilling the remaining binary mixture of meta- and para-tolunitrile to concentrate to more than 75 mol-% para-tolunitrile, and freezing out the para-tolunitrile at below 26° C.

2. A process as claimed in claim 1, wherein the distillation is carried out under pressures of from $10^3$ to $3 \times 10^4$ Pa.

3. A process as claimed in claim 1, wherein a reflux ratio of from 5:1 to 50:1 is employed in the distillation.

4. A process as claimed in claim 1, wherein the ternary mixtures of said isomers are obtained by isomerization of pure ortho-, meta- or para-tolunitrile or mixtures thereof at from 380° to 580° C. on zeolite catalysts.

5. A process as claimed in claim 4, wherein the isomerization is carried out in the gas phase at from 380° to 580° C.

6. A process as claimed in claim 4, wherein the isomerization is carried out in the liquid phase under pressures of from $10^5$ to $10^7$ Pa.

7. A process as claimed in claim 4, wherein alumino or gallium zeolites of the pentasil type are used as zeolite catalysts.

8. A process as claimed in claim 4, wherein alumino or gallium zeolites of the pentasil type with crystal sizes of from 0.05 to 3 μm are used as zeolite catalysts.

9. A process as claimed in claim 4, wherein alumino or gallium zeolites of the pentasil type which have been doped with noble metals or with rare earth metals are used as zeolite catalysts.

* * * * *